(12) United States Patent
Castor et al.

(10) Patent No.: US 8,629,177 B2
(45) Date of Patent: Jan. 14, 2014

(54) NANOENCAPSULATED DELTA-9-TETRAHYDROCANNABINOL

(75) Inventors: Trevor Percival Castor, Arlington, MA (US); Geoffrey Purdum, North Attleboro, MA (US)

(73) Assignee: Aphios Corporation, Woburn, MA (US)

( * ) Notice: Subject to any disclaimer, the term of this patent is extended or adjusted under 35 U.S.C. 154(b) by 105 days.

(21) Appl. No.: 13/216,077

(22) Filed: Aug. 23, 2011

(65) Prior Publication Data

US 2012/0052119 A1 Mar. 1, 2012

Related U.S. Application Data

(60) Provisional application No. 61/402,129, filed on Aug. 24, 2010.

(51) Int. Cl.
*A61K 9/14* (2006.01)
*A61K 31/35* (2006.01)

(52) U.S. Cl.
USPC ............................ 514/454; 514/437; 424/489

(58) Field of Classification Search
USPC ........................ 514/232.8, 437, 454; 424/489
See application file for complete search history.

(56) References Cited

U.S. PATENT DOCUMENTS

2003/0229027 A1* 12/2003 Eissens et al. ................... 514/23
2007/0072939 A1* 3/2007 Kupper .......................... 514/454

OTHER PUBLICATIONS

Holzer, M. et al. "Physico-chemical characterisation of PLGA nanoparticles after freeze-drying and storage", Eur. J. Pham. Biopharm., 72 (2009) 428-437.*
Shekunov, B. et al. ("Engineering of Composite Particles for Drug Delivery Using Supercritical Fluid Technology", Polymeric Drug Delivery II, (2006 ed. by S. Svenson), American Chemical Society, pp. 234-249.*
Vandervoort, J. et al. ("Biocompatible stabilizers in the preparation of PLGA nanoparticles: a factorial design study", Int'l J. Pharm. 238 (2002) 77-92.*

* cited by examiner

*Primary Examiner* — Gina C Justice
(74) *Attorney, Agent, or Firm* — Lathrop & Gage LLP; Anthony J. Janiuk

(57) ABSTRACT

Embodiments of the present invention are directed to articles of manufacture and methods of making such articles having utility for the delivery of cannabinoids as a therapeutic. One embodiment of the present invention directed to the article of manufacture comprises a lyophilized particle or sphere having a diameter of about 100 to 500 nanometers having a shell and comprising a biodegradable polymer containing a cannabinoid. A featured cannabinoid is delta-9-tetrahydrocannabinol (delta-9-THC).

11 Claims, 2 Drawing Sheets

NANOENCAPSULATED DELTA-9-TETRAHYDROCANNABINOL

CROSS REFERENCE TO RELATED APPLICATIONS

This application is a continuation in part of U.S. provisional application Ser. No. 61/402,129 filed Aug. 23, 2010. This application claims priority to such provisional application and incorporates by reference the disclosure therein.

GOVERNMENT SUPPORT

Research leading to this invention was in part funded with Grant No. 1R43DA024552-01 from the National Institute on Drug Abuse, United States National Institutes of Health, Bethesda, Md.

FIELD OF THE INVENTION

The present invention pertains to a product consisting of delta-9-tetrahydrocannabinol (delta 9-THC) encapsulated in biodegradable polymer nanospheres as well as a method of encapsulating delta 9-THC in biodegradable polymer nanospheres.

BACKGROUND OF THE INVENTION

Cannabinoids are considered a drug of abuse. However, certain forms of cannabinoids have therapeutic actions which actions have not been effectively used to date. For example, without limitation, cannabidiol (CBD) which is not psychoactive, has significant anticonvulsant, sedative, and other pharmacological activity. In addition to helping marijuana users overcome their addiction, $\Delta$9-THC has applicability in several other chronic diseases such as cancer pain, AIDS wasting, emesis, cachexia, obesity, smoking cessation, schizophrenia, multiple sclerosis and Parkinson's disease.

Therapeutic uses of cannabinoids has been limited because of social and legal concerns and because means for administering cannabinoids has been lacking. Cannabinoids with therapeutic potential are not particularly stable and degrade readily.

SUMMARY OF INVENTION

Embodiments of the present invention are directed to articles of manufacture and methods of making such articles having utility for the delivery of cannabinoids as a therapeutic. One embodiment of the present invention directed to the article of manufacture comprises a lyophilized sphere or particle having a diameter of about 100 to 500 nanometers having a shell comprising a biodegradable polymer containing a cannabinoid. A featured cannabinoid is delta-9-tetrahydrocannabinol (delta-9-THC).

A featured biodegradable polymer is a polymer of poly (D,L-lactide-coglycolide polymer) and polycaprolactone. A embodiment features poly (D,L-lactide-coglycolide polymer) present in a ratio of 75:25 to 25:75 lactide to glycolide. Other embodiments feature ratios of 60:40 to 40:60 and about 50:50.

The sphere is formed in a deareated buffer and may contain some compounds associated with the buffer. As used herein, the term "deareated buffer" refers to an aqueous solution having an oxygen content lower than a commonly found in tap water or water allowed to stand in an open container for a prolonged period. One embodiment of the present article features a buffer comprises one or more sugars. The sugars are present in the buffer in a concentration of 5 to 20 percent. Another embodiment of the present invention features a buffer comprises an alcohol. The alcohol has a concentration ranging from 1 to 50%. The alcohol can be selected from the group comprising methanol, ethanol, and propanol. A preferred alcohol is ethanol.

As used herein, the buffer is understood to lose much if not all of its alcohol and aqueous content during the lyophilization, leaving non-volatile constituents which return to solution upon solubilization as part of the bio-degradation of the shell and/or the absorbtion of water from the environment.

A further embodiment of the present invention features a cross linking agent. A preferred cross linking agent is polyvinyl alcohol. The concentration of the linking agent is 0.1 to 10% or more preferably about 1%.

As used herein, the term "sphere" is not intended to suggest uniformity in shape, or geometric form. The spheres may have irregularities and be particle-like. The terms sphere and particle are used interchangeably. The term shell is used to denote the outer surface of the sphere or particle.

One embodiment of the present invention features a plurality of spheres in a quantity to cause a therapeutic effect. For example, without limitation, a plurality of spheres is held in a dosage form. The dosage form is selected from the group comprising inhalers, capsules, gel caps, tablets, pills, powders, suspensions, implants and transdermal patches.

A further embodiment of the present invention is directed to a method of making a lyophilized sphere having a diameter of about 100 to 500 nanometers having a shell comprising a biodegradable polymer containing a cannabinoid. The method comprising the steps of forming a mixture of one or more biodegradable polymers and a cannabinoid in carbon dioxide held under conditions in which carbon dioxide is a super critical, critical or near critical fluid. The mixture is injected in a stream in a deareated solution comprising a cross-linking agent in a buffer to form one of more spheres having a diameter of 100 to 500 nanometers. The one or more spheres are lyophilized to form a lyophilized sphere having a diameter of about 100 to 500 nanometers having a shell comprising a biodegradable polymer containing the cannabinoid.

One embodiment features the biodegradable polymer poly (D,L-lactide-coglycolide polymer) and polycaprolactone. One embodiment features the cannabinoid delta-9-tetrahydrocannabinol.

Another embodiment features poly (D,L-lactide-coglycolide polymer) present in a ratio of 75:25 to 25:75, or 60:40 to 40:60, or about 50:50.

One embodiment features a buffer comprises one or more sugars. Preferably, the sugars are present in the buffer in a concentration of 5 to 20 percent. A further embodiment features a buffer comprising an alcohol. Preferably, the alcohol has a concentration ranging from 1 to 50%. A preferred alcohol is ethanol.

One embodiment of the present invention features a cross linking agent, such as, without limitation, polyvinyl alcohol. The cross linking agent is present in the buffer or the spheres are placed in a solution containing the cross linking agent prior to lyophilization.

The present spheres, having diameters measured in nanometers, sometimes referred to as nanoparticles or nano spheres, contain cannabinoids, such as delta-9-tetrahydrocannabinol in an environment having limited oxygen and other reactants which degrade the cannabinoid. The articles of manufacture are stable and bioavailable.

These and other features of the present invention will be apparent to those skilled in the art upon viewing the Figures and reading the detailed description which follow.

DETAILED DESCRIPTION

Embodiments of the present invention will be discussed in detail as to what the inventor considers to be the best mode, with respect to an article of manufacture comprising a lyophilized sphere having a diameter of about 100 to 500 nanometers having a shell comprising poly (D,L-lactide-coglycolide polymer) and polycaprolactone containing delta-9-tetrahydrocannabinol. Those skilled in the art will readily understand that such embodiments are subject to modification and alteration without departing from the teachings herein. Therefore, the invention should not be limited to these precise details.

As used herein, the term "delta-9-tetrahydrocannabinol" or "Δ9-THC" or "Δ9-Tetrahydrocannabinol" is used in the normal chemical sense of a the compound, $C_{21}H_{30}O_2$ (MW=314.46) the only psychoactive constituent of marijuana (hashish); LD50 in Fischer rats (mg/kg): 1,270 (males), 730 (females) orally, sesame oil vehicle; 800 (males) orally, sesame oil, 1% polysorbate 80, saline emulsion; 40 (males, females), i.v.; 105.7 (males, females) inhalation, corrected for particulate losses and pulmonary adsorption to 42 mg/kg. Δ9-THC is a controlled substance. [Merck Index, 13th Edition, p. 1643, 2001].

As used herein, the terms "critical", "supercritical" and "near critical" are used in their physical-chemical sense to mean one or more compounds under conditions that are supercritical, critical or near critical. A pure compound enters its supercritical fluid region at conditions that equal or exceed both its critical temperature and critical pressure. These critical parameters are intrinsic thermodynamic properties of all sufficiently stable pure component compounds. Carbon dioxide, for example, becomes supercritical at conditions that equal or exceed its critical temperature of 31.1° C. and its critical pressure of 72.8 atm (1,070 psig). In the supercritical or near-critical fluid region, normally gaseous substances, such as carbon dioxide, become dense phase fluids that have been observed to exhibit greatly enhanced solvating power as compared to the gaseous state. At a pressure of 3,000 psig (204 atm) and a temperature of 40° C., carbon dioxide has a density around 0.8 g/cc and behaves very much like a nonpolar organic solvent.

The density of supercritical fluid is strongly dependent on both temperature and pressure—temperature changes of tens of degrees or pressure changes by tens of atmospheres can change solubility by an order of magnitude or more.

As used herein, the term "biodegradable" refers to materials that are broken down in the body to nontoxic products (lactic acid and glycolic acid) and have been approved by the FDA for use as resorbable sutures, in bone implants and as controlled release microspheres. The most commonly used bioerodable polymers are of the poly(hydroxyacid) type, in particular poly(L-lactic acid), poly(D,L-lactic acid), poly(g-lycolic acid) and copolymers thereof.

Figure 1:
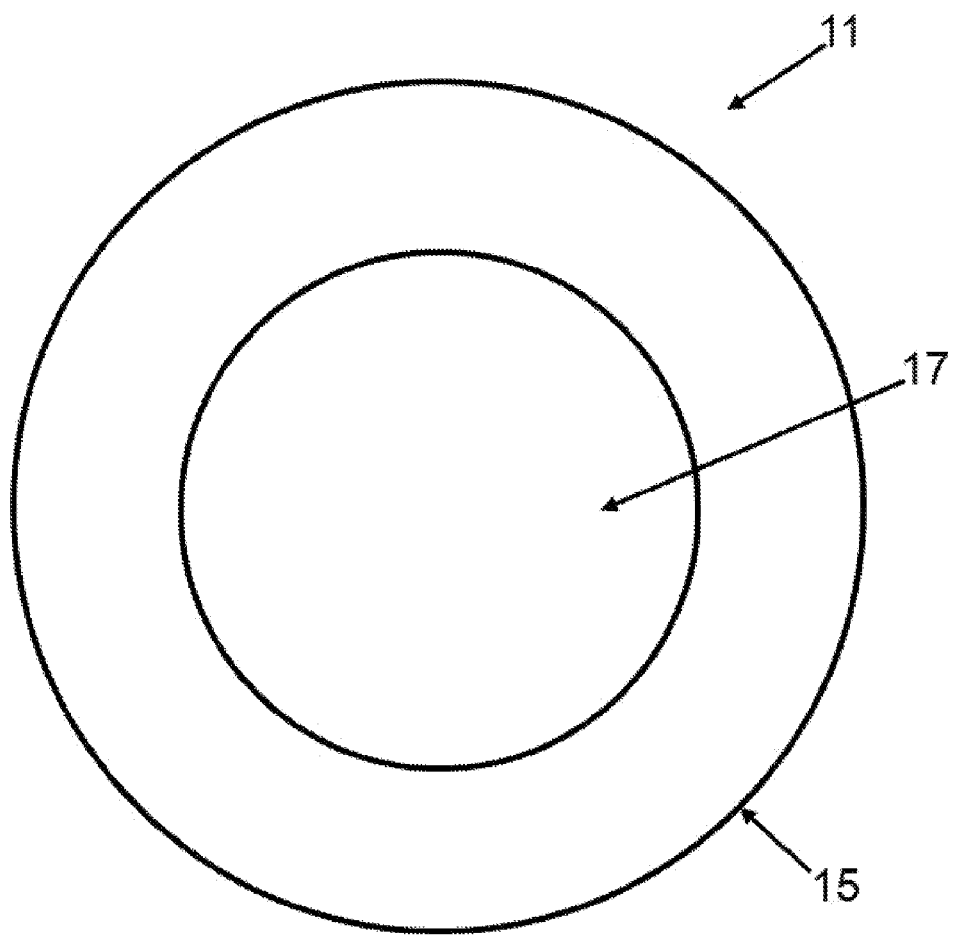
FIG. 1 depicts an article of manufacture having features of the present invention; and, FIG. 2 depicts an apparatus for making embodiments of the present invention and performing features of the present method.
Figure 2:
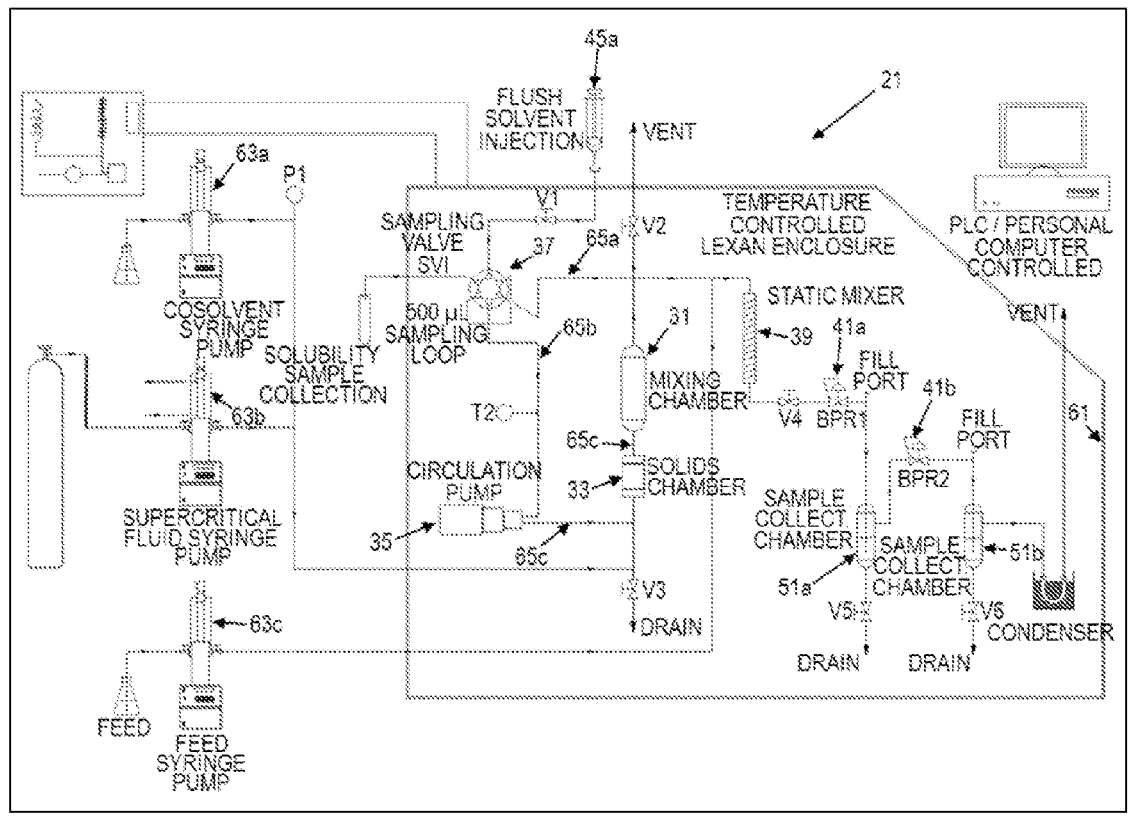

Turning now to FIG. 1, an embodiment of the present invention directed to the article of manufacture, a lyophilized sphere, generally designated by the numeral 11 is depicted in cross-sectional view. The sphere 11 has a diameter of about 100 to 500 nanometers. Although depicted as a sphere, sphere 11 may not be perfect in its geometric form or shape and may have irregularities. Sphere 11 may have particle-like features. The sphere 11 has a shell 15 comprising a biodegradable polymer containing a cannabinoid. The sphere has an interior 17 which comprises the biodegradable polymer, which may or may not be cross linked, and a cannabinoid. A featured cannabinoid is delta-9-tetrahydrocannabinol (delta-9-THC). The shell 15 is cross-linked. To the extent the deareated buffer is incorporated in the sphere 11, the volatile components are substantially lost upon lyophilization. The deareated buffer in this context refers to the non-volatilized components of the buffer, for example, one or more sugars which may migrate into the shell 15 and interior 17 upon formation.

The example feature a polymer of poly (D,L-lactide-coglycolide polymer) and polycaprolactone. Referring now to poly (D,L-lactide-coglycolide polymer), this polymer is present in a ratio of 75:25 to 25:75 lactide to glycolide. Other embodiments feature ratios of 60:40 to 40:60 and about 50:50. The poly (D,L-lactide-coglycolide polymer) and polycaprolactone are used in a ratio of about 2 to 1 to 1 to 2 parts by weight lactide-coglycolide to polylactone. These polymers readily form a solution of about one to one parts by weight.

The deareated buffer is an aqueous solution having a low oxygen. For example, water which has been held under low pressure in the absence of atmospheric gases. One embodiment of the present article features a buffer comprises one or more sugars. The sugars are present in the buffer in a concentration of 5 to 20 percent. Another embodiment of the present invention features a buffer comprises an alcohol. The alcohol has a concentration ranging from 1 to 50%. The alcohol can be selected from the group comprising methanol, ethanol, and propanol. A preferred alcohol is ethanol.

Again, the buffer loses most of its alcohol and aqueous content during the lyophilization, leaving non-volatile constituents which return to solution upon solubilization as part of the bio-degradation of the particle or sphere and/or the absorbtion of water from the environment.

The shell 15 has a cross linking agent. A preferred cross linking agent is polyvinyl alcohol. The concentration of the linking agent in the buffer or in a shell forming solution is 0.1 to 10% or more preferably about 1%.

A plurality of spheres is held in a dosage form [not shown] in a quantity to cause a therapeutic effect. The dosage form is selected from the group comprising inhalers, capsules, gel caps, tablets, pills, powders, suspensions, implants and transdermal patches.

A further embodiment of the present invention is directed to a method of making a lyophilized sphere 11 having a diameter of about 100 to 500 nanometers having a shell 15 comprising a biodegradable polymer containing a cannabinoid. The method comprising the steps of forming a mixture of one or more biodegradable polymers and a cannabinoid in carbon dioxide held under conditions in which carbon dioxide is a supercritical, critical or near critical fluid. The mixture is injected in a stream in a deareated solution comprising a cross-linking agent in a buffer to form one of more spheres having a diameter of 100 to 500 nanometers. The one or more spheres are lyophilized to form a lyophilized sphere having a diameter of about 100 to 500 nanometers having a shell comprising a biodegradable polymer containing the cannabinoid.

An apparatus, generally designated by the numeral 21, for performing an embodiment of the present invention, is depicted in FIG. 21. The apparatus 11 21 has the following major components: a mixing chamber 31, a solids chamber 33 for containing the polymer(s), a high pressure circulation pump 35, a multi-port sampling valve 37 (Valco), a static in-line mixer 39, two back pressure regulators 41a and 41b (BPR), two injectors 45a and 45b, and two sample collection chambers 51a and 51b all contained in a temperature controlled chamber 61. External to this chamber, three syringe pumps 63a, 63b and 63c (Isco, Inc., Lincoln, Nebr.), are used for delivery of the supercritical fluid, cosolvent and Δ9-THC solution. The mixing chamber 31, solids chamber 33, circulation pump 35 and sampling valve 37 are connected in a high-pressure circulation loop represented by conduits 65a, 65b and 65c (and intervening fluid components) with a total volume of approximately 160 ml. The outlets of the supercritical fluid and cosolvent syringe pumps 63a and 63b are connected at a mixing tee and fed into the high-pressure circulation loop at the entrance of the solids chamber.

There are two take-offs from the high-pressure circulation loop. The first take-off can be achieved by switching the sample valve 37 to allow the circulating stream to flow through a 500 microliters-sampling loop. After the sample is trapped, the sampling loop is flushed with a liquid solvent such as acetone to collect the polymer dissolved in 500 microliters of supercritical, critical or near critical carbon dioxide with or without cosolvents such as an alcohol. The second take-off from the high-pressure circulation loop is at the top of the mixing chamber 31. This take-off is connected to the inlet of static in-line mixer 39. The feed syringe pump for a cannabinoid rich stream is connected to the inlet of the static in-line mixer 39.

In the alternative, second chamber [not shown] is added to the high-pressure circulation loop to contain cannabinoid. Or, as a further alternative, cannabinoid is added directly to the polymer in the solids chamber 33. Sample collection chambers 51a and 51b have a 10-mil (internal diameter of 0.25 mm or 250 micron) capillary injection nozzle. Larger internal diameter 316 stainless steel capillary tubes can be used to manufacture larger particle sizes. Impingement nozzles (Bete Fog Nozzle, Inc., Greenfield, Mass.) can also be used. Nozzle impingement will prevent the coagulation of polymeric particles resulting from high concentrations of polymer particles formed under rapid flow conditions.

The apparatus 21 is maintained as a closed system. The entire apparatus up to the backpressure regulators 41a and 41b is designed to operate up to 5,000 psig and 60° C. The apparatus 21 is cleaned in-place by washing with a series of solvents including bleach, caustic and dilute hydrochloric acid, and then sterilized in-place with an ethanol/water (70/30) mixture.

Biodegradable polymers used in the following examples include pharmaceutical-grade Resomer® RG-502 [poly (D,L-lactide-co-glycolide) 50:50] polymer (Boehringer Ingelheim KG). Specifications are presented in Table 1.

TABLE 1

Specifications of Resomer ® RG 502 PLGA Polymer

| Chemical formula | Polymer Composition | Inherent Viscosity (dL/g) | Glass transition range (° C.) |
|---|---|---|---|
| $(C_3H_4O_2)_n(C_2H_2O_2)_m$ | Poly (D,L-lactide-co-glycolide) 50:50 | 0.16-0.24 | 40-55 |

Pegylated PLGA will impact both the rate of uptake in the stomach and the circulation time of the nanoencapsulated Δ9-THC in the body. Polyethylene glycols (PEGs) are non-toxic and amphophilic, i.e. soluble both in both water and most organic solvents. In pegylation, polyethylene glycols are covalently attached to PLGA, increasing the size of the molecule so it is less likely secreted through the kidney while protecting the Δ9-THC from degradation. In addition to increasing biological half-life, pegylation would improve stability and water solubility, and immunologic characteristics. There may be a trade-down in improving water solubility in that controlled release may be adversely impacted. Specifications of the pegylated PLGA polymers are listed in Table 2.

TABLE 2

Specifications for Pegylated PLGA

| Type | Inherent Viscosity (dL/g) | DL-lactide/glycolide mole ratio |
|---|---|---|
| RGP t 50106 | Triblock | 10% PEG with 6,000 Dalton |
| RGP d 5055 | Diblock | 5% PEG with 5,000 Dalton |
| RGP d 50105 | Diblock | 10% PEG with 5,000 Dalton |
| RGP d 50155 | Diblock | 15% PEG with 5,000 Dalton |

RG: polyester part (A)-poly(DL-lactide-glycolide) 50:50 ratio
P: PEG (B)

Polymer nanospheres/nanoparticles are formed by injecting the polymer-rich, cannabinoid laden carbon dioxide fluid with one or more entrainers such as an alcohol into a 1% polyvinyl alcohol (PVA) deareated buffer solution. The buffer preferably contains a sugar such as sucrose. Other media such as high concentration sucrose solutions to aid in particle stability during lyophilization, liquid nitrogen for freezing the particles and phosphate-buffered saline at physiological pH as a control can be used. Other collection media parameters that impact the size and uniformity of the nanospheres are temperature and pressure. Lower temperatures are much more favorable for polymer and Δ9-THC stabilities. Operating pressure as well as pressure in the particle formation chamber control the size and uniformity of bubbles formed and nanospheres generated. The pressure in the particle formation chamber can be varied from the vapor pressure of the neat supercritical, critical or near critical fluid at the temperature of the medium to atmospheric pressure.

Optimum polymer nanospheres formation, size and Δ9-THC encapsulation depend on the ratio of polymer to Δ9-THC in the sample collection chamber(s). This ratio depends on the flowrate of the Δ9-THC-rich stream and its concentration, and the flowrate of the polymer-rich supercritical, critical or near critical fluid stream and its concentration (which is defined by polymer solubility at operating conditions). The polymer: Δ9-THC acid ratio can be varied from 100:1 to 1:1. Should there be problematic aggregation of the polymer nanospheres after their formation, the agglomeration is broken by disaggregated utilizing protein nanoparticles.

Characterization, In Vitro Dissolution and Release Studies and Stability Evaluation Δ9-THC Biodegradable Polymer Nanospheres: Conventional light microscopy and photomicrography was utilized to characterize the Δ9 THC biodegradable polymer nanospheres. Routine size determinations were based on observations made through a Reichert-Jung Microstar IV microscope with a calibrated reticule. To provide a further record, photographic slides were made for a number of viewings with a Reichert-Jung Photostar Automatic Camera System.

Particle Size: Particle sizes and distributions of the formulations were determined by laser beam interferometer, using a Coulter 4MD submicron particle size analyzer with a range of 30 Angstroms to 3 microns. This technique utilizes photon correlation spectroscopy of the Brownian motion of particles suspended in a liquid to determine the particle size. Multiple-angle detection on the 4MD allows for better characterization of polydisperse samples. These analyses provide: (i) unimodal size analyses that have only mean size and standard deviation; (ii) size distribution analyses that yield information about polydispersity of the sample; and (iii) for the Coulter N4 Plus, "fingerprint," a procedure that uses the multiple angle measurement provided by the instrument to detect contamination of a sample by particles larger or smaller than the main distribution.

Δ9-THC Analytical Method: Two HPLC methods developed by Aphios can be used: (1) a gradient system utilizing a modified Phenomenex method; and (2) an isocratic system that is a modification of the Maripharm, Rotterdam, Netherlands method. The latter system is based on peak separation and product purities. This isocratic method utilized a Phenomenex Luna 3 μm C18 column (5 cm×4.6 mm) with a pre-column at 25° C. The mobile phase, at 1.0 ml/min, consists of 78% methanol:22% water containing 1% acetic acid. Absorbance was monitored by a Waters Photodiode Array (PDA) detector, Model 996, and measured at 285 nm and 230 nm. The analytical HPLC system includes a Waters 717 Autosampler, 600E System Controller and a Waters Dual-Piston High Pressure HPLC pump, Model No. 600, driven by a Pentium 4 Personal Computer and controlled by Waters Millennium 4.0 software. Temperature of the HPLC column is controlled by an Eppendorf CH-30 column heater. Standards are run on the developed HPLC protocol to establish standard regression curves, limits of quantification, and purity of the Δ9-THC. The purities of the standards and samples are determined using Millennium Software for: (1) Peak Purity Testing which compares all spectra within a peak to the peak apex spectrum to determine if a peak is spectrally homogeneous from liftoff to touchdown; (2) Multicomponent Peak Purity Testing which performs iterative peak purity comparisons to evaluate if there are multiple, spectrally distinct compounds in a peak; and (3) Library Matching which compares an unknown (peak apex) spectrum to known standard spectra in a library to identify a compound.

Dissolution Characteristics: In vitro dissolution were conducted to determine the rate at which the untreated Δ9-THC polymer nanospheres will dissolve. Ideally, an in vitro dissolution test should reflect the in vivo solubilization conditions. Real in vivo conditions are complex and may include particle-particle interactions that lead to particle aggregation, position dependent permeability and metabolism, changing pH, luminal content and hydrodynamics in the GI tract.

Stability Studies: Shelf stability studies were conducted with Δ9-THC, Δ9-THC polymer nanospheres and formulations of the aforementioned. The following tests were performed: (i) physical appearance; and (ii) Δ9-THC content and integrity. Statistical analysis of the data sets were performed using SYSTAT®.

Encapsulation Efficiency: The loading efficiency of Δ9-THC in polymer nanospheres were determined by dissolving a known amount of nanospheres in a 90% acetonitrile aqueous solution. The amount of Δ9-THC were determined by HPLC assay, and the loading efficiency was calculated based on weight percent.

In Vitro Release Studies: In vitro release kinetics of nanospheres were carried out by placing a sample of nanospheres in PBS buffer (pH=7.4), simulated gastric fluid and plasma at 25° C. and 37° C. At intervals of minutes, hours and days, samples were taken and 9-THC were measured by HPLC in triplicate. Relating the amount of Δ9-THC in the supernatant to the total amount in the sample of nanospheres allows determination of cumulative Δ9-THC released as a function of time.

EXAMPLES

Example 1

Δ9-THC Calibration Curves

A calibration curve was prepared for the encapsulation of Δ9-THC assays. Column: Phenomenex Luna C-181; 150×4.6 mm; 5 μm; Flowrate: 1.0 mL/min; Temperature: 30° C.; Mobile Phase: 95% MeCN in H2O; Injection Volume: 20 μL; and Run Time: 10 min.

The Δ9-THC standard has a large absorbance at 210 nm and a lower one at 285 nm. The retention time is 3.9 min. When measuring at 285 nm two other more strongly absorbing compounds elute prior to Δ9-THC at 3.1 min and 3.3 min. However when measuring at 210 nm, these two impurities have much less absorbance than Δ9-THC and are very minimal in the scan.

Two calibration curves were prepared, one at 285 nm which shows the impurities, but is less sensitive towards Δ9-THC and one at 210 nm, which is very sensitive for Δ9-THC. One vial that was prepared during the aliquoting of the Δ9-THC was used (the aliquot that remained that had only 0.75 mL at 1 mg/mL). The data for the 285 nm calibration curve is listed in Table 3 and the 285 nm calibration curve. The data for the 210 nm calibration curve is listed in Table 4.

TABLE 3

Delta-9 THC Standard Curve Measured at 285 nm.

| Initial concentration (mg/mL) | volume (SM) (mL) | Volume EtOH (mL) | Final Volume (mL) | Final concentration (mg/mL) | Area |
|---|---|---|---|---|---|
| 1 | 0.5 | 1 | 1.5 | 0.333333333 | 1212088 |
| 1 | 0.2 | 1.3 | 1.5 | 0.133333333 | 470165 |
| 0.333333 | 0.3 | 1.2 | 1.5 | 0.0666666 | 229534 |
| 0.133333 | 0.3 | 1.2 | 1.5 | 0.0266666 | 91580 |
| 0.066666 | 0.3 | 1.2 | 1.5 | 0.0133332 | 44948 |
| 0.026666 | 0.3 | 1.2 | 1.5 | 0.0053332 | 17963 |
| 0.013333 | 0.3 | 1.2 | 1.5 | 0.0026666 | 8494 |
| 0.005333 | 0.3 | 1.2 | 1.5 | 0.0010666 | 3241 |
| 0.002666 | 0.3 | 1.2 | 1.5 | 0.0005332 | 1680 |
| 0.001066 | 0.3 | 1.2 | 1.5 | 0.0002132 | 0 |
| 0.000533 | 0.3 | 1.2 | 1.5 | 0.0001066 | 0 |

TABLE 4

Delta-9 THC Standard Curve Measured at 210 nm
(Bolded sample used as the standard for quantitation)

| Initial concentration (mg/mL) | volume (SM) (mL) | Volume EtOH (mL) | Final volume (mL) | Final concentration (mg/mL) | Area |
|---|---|---|---|---|---|
| 1 | 0.5 | 1 | 1.5 | 0.333333333 | 33612027 |
| 1 | 0.2 | 1.3 | 1.5 | 0.133333333 | 20322517 |
| 0.333333 | 0.3 | 1.2 | 1.5 | 0.0666666 | 10463669 |
| 0.133333 | 0.3 | 1.2 | 1.5 | 0.0266666 | 4187866 |
| 0.066666 | 0.3 | 1.2 | 1.5 | 0.0133332 | 2053488 |
| 0.026666 | 0.3 | 1.2 | 1.5 | 0.0053332 | 805173 |
| 0.013333 | 0.3 | 1.2 | 1.5 | 0.0026666 | 396700 |
| 0.005333 | 0.3 | 1.2 | 1.5 | 0.0010666 | 155947 |

TABLE 4-continued

Delta-9 THC Standard Curve Measured at 210 nm
(Bolded sample used as the standard for quantitation)

| Initial concentration (mg/mL) | volume (SM) (mL) | Volume EtOH (mL) | Final volume (mL) | Final concentration (mg/mL) | Area |
|---|---|---|---|---|---|
| 0.002666 | 0.3 | 1.2 | 1.5 | 0.0005332 | 76819 |
| 0.001066 | 0.3 | 1.2 | 1.5 | 0.0002132 | 30531 |
| 0.000533 | 0.3 | 1.2 | 1.5 | 0.0001066 | 16544 |

Example 2

Δ9-THC Nanoencapsulation with Carbon Dioxide and Ethanol Cosolvent

Δ9-THC was encapsulated in PLGA polymer nanospheres using SFS carbon dioxide and ethanol cosolvents with different concentrations of cosolvents. In each experiment, the polymer and Δ9-THC enriched SuperFluids stream was decompressed into a 1% PVA solution.

TABLE 5

Δ9-THC Nanoencapsulation Experiments with SuperFluids CO2 with Ethanol Cosolvent

| | THC-07 | | THC-08 | | THC-09 | | THC-10 | |
|---|---|---|---|---|---|---|---|---|
| Critical Fluid | CO2 | | CO2 | | CO2 | | CO2 | |
| Cosolvent | Ethanol | | Ethanol | | Ethanol | | Ethanol | |
| Pressure (psig) | 2,500 | | 2,500 | | 2,500 | | 2,500 | |
| Temperature (° C.) | 45 | | 45 | | 45 | | 45 | |
| % Cosolvent | 10 | | 5 | | 0 | | 5 | |
| Nozzle Diameter (thousandths) | 30 | | 30 | | 30 | | 10 | |
| Product 1 (mg)\|particle size (nm) | 0.489 | 736 | 0.504 | 513 | 0.17 | 327 | 0.334 | 390 |
| Product 2 (mg)\|particle size (nm) | 0.188 | 404 | 0.0224 | 297 | 0.0499 | 261 | 0.037 | 290 |
| Product 3 (mg)\|particle size (nm) | 0.038 | 285 | 0 | 308 | 0 | 263 | 0 | 269 |

Example 3

Δ9-THC Nanoencapsulation with Carbon Dioxide and Ethanol Cosolvent for Different Nozzle Sizes Δ9-THC was encapsulated in PLGA polymer nanospheres using SFS carbon dioxide and ethanol cosolvents with different concentrations of cosolvents. In each experiment, the polymer and Δ9-THC enriched SuperFluids stream was decompressed into a 1% PVA solution.

TABLE 6

Δ9-THC Nanoencapsulation Experiments with SuperFluids CO2 with Ethanol Cosolvent for Different Nozzle Sizes

| | THC-08 | | THC-10 | |
|---|---|---|---|---|
| Critical Fluid | CO2 | | CO2 | |
| Cosolvent | Ethanol | | Ethanol | |
| Pressure (psig) | 2,500 | | 2,500 | |
| Temperature (° C.) | 45 | | 45 | |
| % Cosolvent | 5 | | 5 | |
| Nozzle Diameter (thousandths) | 30 | | 10 | |
| Product1 (mg)\|particle size (nm) | 0.504 | 513 | 0.334 | 390 |

TABLE 6-continued

Δ9-THC Nanoencapsulation Experiments with SuperFluids CO2 with Ethanol Cosolvent for Different Nozzle Sizes

| | THC-08 | | THC-10 | |
|---|---|---|---|---|
| Product2 (mg)\|particle size (nm) | 0.0224 | 297 | 0.037 | 290 |
| Product3 (mg)\|particle size (nm) | 0 | 308 | 0 | 269 |

Example 4

Nanoencapsulation Optimization Studies

Twenty three (23) experiments were performed with different fluids at pressures and temperatures guided by thermodynamic analyses and solubility experiments also varied were the mode of operation, constant pressure versus varying pressure and the composition and concentration of the collection buffer.

TABLE 7

Polymer Nanoencapsulation of Δ9-THC in SuperFluids ™ CO2:Ethanol::85%:15% at 2,500 psig and 45° C. in 10% Sucrose/40% Ethanol/0.1% PVA Deareated Buffer at pH = 4.0 after Lyophilization (THC-19)

| Run No. | SFS | Temp. (° C.) | Pressure (psig) | Particle Size (nm) | Concentration (mg/100 mL) | Percent Encapsulation |
|---|---|---|---|---|---|---|
| THC-19 | 85% CO$_2$: 15% Ethanol | 45 | 2,500 | 287 | 1.908 | 49.7 |

TABLE 8

Polymer Nanoencapsulation of Δ9-THC in SuperFluids ™ CO2:Acetone::95%:5% at 2,500 psig and 45° C. in 10% Sucrose/40% Ethanol/0.1% PVA Deareated Buffer at pH = 4.0 after Lyophilization (THC-21)

| Run No. | SFS | Temp. (° C.) | Pressure (psig) | Particle Size (nm) | Concentration (mg/100 mL) | Percent Encapsulation |
|---|---|---|---|---|---|---|
| THC-21 | 95% CO$_2$ 5% Acetone | 45 | 2,500 | 230 | 2.692 | 81.9 |

THC-19 and THC-21 were conducted in the constant pressure mode and used a collection buffer comprised of 40% ethanol, 10% sucrose, and 0.1% PVA at pH=4.0. This solution was degasified using nitrogen and helium purges.

As an alternative to SFS CO2, we optimized the use of SFS Freon-22 in THC-22, increasing the amount of Δ9-THC and polymer by about 10-fold to increase drug loading (Table 9).

TABLE 9

Polymer Nanoencapsulation of Δ9-THC in
SuperFluids ™ Freon 22 at 3,000 psig and 25° C. in
10% Sucrose/40% Ethanol/0.1% PVA Deareated Buffer at pH = 4.0 after
Lyophilization (THC-22)

| Run No. | SFS | Temp. (° C.) | Pressure (psig) | Particle Size (nm) | Concentration (mg/100 mL) | Percent Encapsulation |
|---|---|---|---|---|---|---|
| THC-22 | Freon-22 | 25 | 3,000 | 226 | 9.688 | 69.6 |

THC-22 particle size after lyophilization was 325 nm and the recovery efficiency after lyophilization was 91%.

Example 5

Composition of Buffer

The composition of the buffer was determined from stability studies with Δ9-THC at different conditions. From six (6) day studies of 0%, 20%, 30% and 40% ethanol in 10% sucrose/0.1% PVA solution, it was found that the drug degrades in the PVA-sucrose solution but is stable if 40% ethanol is introduced. Since PLGA does not dissolve in ethanol, nanoparticles will remain unchanged. Stability experiments were also conducted with Δ9-THC at pH=4, 7 and 10. These experiments determined that Δ9-THC was most stable at pH=4. Experiments were also used to determine that a low concentration of PVA was adequate for cross-linking the polymer and minimizing foaming in the collection buffer. The buffer was deareated to remove dissolved oxygen since Δ9-THC is very sensitive to oxygen. A 10% sucrose buffer was utilized based on prior experimental data for this and other projects to preserve particle integrity after lyophilization. Prior to lyophilization, these products were placed in a −80° C. freezer until they were frozen solid. Samples were then lyophilized for a 24 hour period. These samples were reconstituted in distilled, degasified water and were analyzed using HPLC and particle size analysis via dynamic light scattering. After lyophilization, particle sizes of THC-19 and THC-21 were reduced to 287 and 230 nm respectively, and the recovery efficiencies were 77% and 95% respectively.

Example 6

Stability of Nanoencapsulated Δ9-THC and Naked Δ9-THC

Stability studies were conducted on polymer nanoencapsulated Δ9-THC (THC-12-1) and naked Δ9-THC samples over a 6-week period at 4° C., 25° C. and 40° C. These results indicate that almost 85% of the Δ9-THC content of the nanoencapsulated Δ9-THC is retained in the samples stored at 4° C. over a 6-week period. The results indicate that the Δ9-THC degrades almost equally at each temperature. After 6 weeks most of the Δ9-THC is degraded. Data indicates that nanoencapsulation has significantly improved the stability of Δ9-THC, especially at 4° C.

Example 7

Stability of Nanoencapsulated Δ9-THC in an Acidic Environment

The pH of the gastrointestinal tract changes is similar to a gradient. In the stomach, the pH ranges from 1 to 3 pH units depending on the fastness state, whereas the duodenum has a pH of around 6. Further down the small intestine, the ileum and jejunum have pH values closer to 7-7.5. The transit time in the stomach is 0.5 to 1 hour and the transit time to the jejunum is 2 to 4 hours. To ensure stability in a fasted stomach, the stability of Δ9-THC in THC-22-1 nanoparticles was evaluated at pH ~1.0 and 37° C. to simulate stomach conditions. The amount of Δ9-THC is relatively constant throughout the entire 4-hour period at 37° C. and pH=1.04. The data suggests that the polymer shell should not degrade in the stomach as it makes it way to the small intestine and the product should remain intact.

Example 8

In Vitro Release into Human Plasma

In vitro release studies were conducted with nanoencapsulated Δ9-THC (THC-22-1) into human plasma. Pooled human plasma was purchased from Innovative Research, Novi, Mich. The results indicate that there is diffusional release for about 2½ hours and burst release at about 3½ hours, which may coincide with the half-life of the product.

Example 9

Polymer Nanospheres Formulations

Polymer-drug nanospheres are made with traditional tablet forming excipients and compressed into tablet form or suspended in biocompatible solvents for oral delivery.

Example 10

Liquid Suspension Dosage Form

Polymer nanospheres are suspended in olive oil prior to encapsulation into Size 2 to Size 00 hard- or softgel capsules depending on the dosage levels and the concentration of suspended particles. Such suspensions and encapsulation will facilitate the oral presentation of the drug, prevent particle aggregation or clumping and could further enhance oral bioavailability.

While this invention has been particularly shown and described with references to specific embodiments, it will be understood by those skilled in the art that various changes in form and details may be made therein without departing from the spirit and scope of the invention as defined by the appended claims.

The invention claimed is:

1. A method of making a lyophilized particle or sphere having a diameter of about 100 to 500 nanometers having a shell comprising poly (D,L-lactide-coglycolide polymer) or polycaprolactone containing delta-9-tetrahydrocannabinol, said method comprising the steps of forming a mixture of poly (D,L-lactide-coglycolide polymer) or polycaprolactone containing delta-9-tetrahydrocannabinol in carbon dioxide held under conditions in which carbon dioxide is a supercritical, critical or near critical fluid, injecting said mixture in a stream in a deareated solution comprising a cross-linking agent in a buffer to form one of more particles or spheres having a diameter of 100 to 500 nanometers and lyophilizing said one or more particles or spheres to form a lyophilized particle or sphere having a diameter of about 100 to 500 nanometers having a shell and comprising poly (D,L-lactide-coglycolide polymer) or polycaprolactone containing delta-9-tetrahydrocannabinol.

2. The method of claim 1 wherein said poly (D,L-lactide-coglycolide polymer) is present in a ratio of 75:25 to 25:75.

3. The method of claim 2 wherein said ratio is 60:40 to 40:60.

4. The method of claim 2 wherein said ratio is about 50:50.

5. The method of claim 1 wherein said buffer comprises one or more sugars.

6. The method of claim 5 wherein said sugars are present in said buffer in a concentration of 5 to 20 percent.

7. The method of claim 1 wherein said buffer comprises an alcohol.

8. The method of claim 7 wherein said alcohol has a concentration ranging from 1 to 50%.

9. The method of claim 8 wherein said alcohol is ethanol.

10. The method of claim 1 further comprising a cross linking agent.

11. The method of claim 10 wherein said cross linking agent is polyvinyl alcohol.

* * * * *